United States Patent [19]
Hunter et al.

[11] Patent Number: 5,810,800
[45] Date of Patent: Sep. 22, 1998

[54] ABSORBENT ARTICLE HAVING FLEXURE RESISTANT ELASTICIZED CUFFS

[75] Inventors: Allison Kay Hunter, West Chester; Kimberly Ann Buck, Reading; Ronald Ray McFall, West Chester; Patricia Lee Lampson, Cincinnati, all of Ohio

[73] Assignee: The Procter & Gamble Company, Cincinnati, Ohio

[21] Appl. No.: 671,424

[22] Filed: Jun. 27, 1996

[51] Int. Cl.⁶ ............................. A61F 13/15; A61F 13/20
[52] U.S. Cl. ................. 604/385.2; 604/387; 604/358
[58] Field of Search ................... 604/385.1, 385.2, 604/378, 383, 358

[56] References Cited

U.S. PATENT DOCUMENTS

| | | | |
|---|---|---|---|
| Re. 34,920 | 4/1995 | Aziz et al. | |
| 3,575,174 | 4/1971 | Mogor | 128/290 |
| 4,579,556 | 4/1986 | McFarland | 604/385 |
| 4,678,527 | 7/1987 | Ulman | 156/213 |
| 4,701,177 | 10/1987 | Ellis et al. | 604/385 |
| 4,738,677 | 4/1988 | Foreman | 604/385 |
| 4,758,241 | 7/1988 | Papajohn | 604/387 |
| 4,770,657 | 9/1988 | Ellis et al. | 604/385 |
| 4,816,025 | 3/1989 | Foreman | 604/385.2 |
| 4,834,739 | 5/1989 | Linker, III et al. | 604/385.1 |
| 4,854,984 | 8/1989 | Ball et al. | 156/73.5 |
| 4,944,735 | 7/1990 | Mokry | 604/385.2 |
| 5,026,364 | 6/1991 | Robertson | 604/385.1 |
| 5,032,121 | 7/1991 | Mokry | 604/385.2 |
| 5,074,856 | 12/1991 | Coe et al. | 604/385.1 |
| 5,234,422 | 8/1993 | Sneller et al. | 604/385.2 |
| 5,246,431 | 9/1993 | Minetola et al. | 604/385.1 |
| 5,268,224 | 12/1993 | DesMarais et al. | 604/369 |
| 5,304,160 | 4/1994 | Igaue et al. | 604/385.1 |
| 5,308,346 | 5/1994 | Sneller et al. | 604/385.2 |
| 5,312,386 | 5/1994 | Correa et al. | 604/379 |
| 5,346,486 | 9/1994 | Osborn, III et al. | 604/385.1 |
| 5,387,210 | 2/1995 | Murakami | 604/396 |
| 5,413,569 | 5/1995 | Yamamoto | 604/385.2 |
| 5,490,847 | 2/1996 | Correa et al. | 604/387 |
| 5,518,801 | 5/1996 | Chappell et al. | 604/393 |
| B1 4,589,876 | 4/1993 | Van Tillburg | 604/385.1 |

FOREIGN PATENT DOCUMENTS

| | | |
|---|---|---|
| H 5-86323 | 11/1993 | Japan . |
| WO 95/03765 | 2/1995 | WIPO . |
| WO/96/23471 | 8/1996 | WIPO . |

*Primary Examiner*—John G. Weiss
*Assistant Examiner*—Ki Yong O
*Attorney, Agent, or Firm*—Edward J. Milbrada; Jeffrey V. Bamber; Steven W. Miller

[57] ABSTRACT

Disclosed is an absorbent article, such as a sanitary napkin, incontinent device, or the like. The absorbent article comprises a liquid pervious topsheet, a liquid impervious backsheet, and an absorbent core disposed between the topsheet and the backsheet. The absorbent article further comprises a pair of longitudinally extending cuffs disposed on the body surface of the topsheet on each side of a longitudinal centerline of the absorbent article The cuffs comprise an elastic member and a resilient member and are joined to at least one of the topsheet and the backsheet in a longitudinally elastically elongated state. The elastic member preferably comprises first and second regions which are visibly distinct from each other. The first region comprises at least two substantially planar portions and the second comprises a plurality of raised, rib-like elements. In a particularly preferred embodiment of the present invention, at least one of the substantially planar portions of the first region of the bands of web material extends in a substantially longitudinal direction and at least one other of the substantially planar portions of the first region of the elastic member is oriented at an angle with respect to the longitudinal direction. The resilient member is soft yet sufficiently resilient to resist the compressive forces applied to the cuffs by normal wearer movement. The resilient member is positioned sufficiently close to the body surface of the topsheet to also provide resistance to bending that may also be caused by normal bodily movements.

15 Claims, 9 Drawing Sheets

ABSORBENT ARTICLE HAVING FLEXURE RESISTANT ELASTICIZED CUFFS

FIELD OF THE INVENTION

This invention relates to disposable absorbent articles such as sanitary napkins, incontinent devices, and the like. More particularly, this invention is directed to a sanitary napkin having cuffs for preventing lateral flow of bodily fluids, such as menses.

BACKGROUND OF THE INVENTION

As is well known, a disposable absorbent article, such as a sanitary napkin, has a liquid pervious topsheet, a liquid impervious backsheet, and an absorbent core disposed between the topsheet and the backsheet. Such an absorbent article should conform to the wearer's urogenital region, and be able to prevent leakage of bodily fluids, particularly in the lateral direction. One means of reducing leakage and conforming to a wearer's urogenital region is to provide for the absorbent article to be cup-shaped during use. Such absorbent articles can be further provided with cuffs to provide a barrier for reduction of lateral leakage of bodily fluids.

Such approaches are known to the art. For example, one means for making the absorbent article cup-shaped and forming cuffs, as stated above, is to shape the topsheet, the core and the backsheet themselves such that the absorbent article takes the cup-like form, and the topsheet and/or the backsheet forms the cuffs on both sides of the longitudinally central portion of the absorbent article. Such formed absorbent articles are described in U.S. Pat. No. 3,575,174, U.S. Pat. No. 4,678,527, and U.S. Pat. No. 4,834,739. Absorbent articles of this type have problems such as: 1) increased manufacturing cost because the topsheet, the core and the backsheet have to be shaped to a required form and (2) the free end of the cuff contacts the wearer's skin and may cause wearer discomfort when such an absorbent article is worn because the portion comprising the cuff has no stretch properties.

A second approach to making an absorbent article cup-shaped and forming the cuffs is to join band-like elastic pieces, in an elastically elongated state, to the topsheet and/or the backsheet adjacent both longitudinal edges of the absorbent article. The use of a rubber strip or a thermoplastic elastomeric strip as the band-like elastic piece has been proposed. Such absorbent articles are described in U.S. Pat. No. 4,579,556, U.S. Pat. No. 4,701,177, U.S. Pat. No. 4,758,241, U.S. Pat. No. 4,770,657, U.S. Pat. No. 4,944,735, U.S. Pat. No. 5,032,121, U.S. Pat. No. 5,074,856, and U.S. Pat. No. 5,312,386. In an absorbent article equipped with such band-like elastic pieces, the topsheet, core, and backsheet are shaped like a cup, and the topsheet and/or the backsheet forms the cuffs, due to the contracting action of the band-like elastic pieces. While the stretch properties of absorbent articles of this second type result in improved comfort during wear when compared to absorbent articles of the first type, such absorbent articles are expensive to produce because: (1) the use of a band-like elastic piece made from a relatively expensive rubber or thermoplastic elastomeric is required, (2) additional material is required to accommodate the band-like elastic pieces. Further, such cuffs tend to become flattened (with a resulting increase in risk of leakage) as the absorbent article is pulled to a more flat-out configuration such as may happen with increasing wearer body dimensions.

A third approach for making the absorbent article cup-shaped and forming the cuffs is to thermally bond the longitudinally opposite ends and the laterally outward portion of a thermoplastic elastic piece, in an elastically elongated state, to appropriate sites on the upper surface of the topsheet. The topsheet is also joined, as required, to the core and the backsheet. In an absorbent article equipped with such elastic pieces, the topsheet, core and backsheet are shaped like the cup due to the contracting action of the elastic pieces. On both sides of the longitudinal central portion, the elastic pieces are caused to extend upwardly inclinedly in a widthwise inward direction, forming the cuffs. Such a third proposal is disclosed in Japanese Laid-Open Utility Model Publication No. 86323/93. In this type of absorbent article, the thermoplastic elastic pieces themselves, which are thermally bonded to the topsheet, form cuffs on both sides of the longitudinal centerline. Moreover, thermal bonding can be carried out relatively simply. Thus, manufacturing cost will be lower than either of the first two types of absorbent articles. However, such absorbent articles may be uncomfortable when they are worn because the elastic material is a film which can occlude a relatively large portion of a wearer's skin. Further, thermoplastic, elastic materials are relatively expensive when compared to other components of the absorbent article and, because they are a different material than the topsheet, they are sometimes difficult to thermally bond to the other components of the absorbent article. Both of these aspects tend to increase manufacturing cost.

While the above described references provide a cup-shaped absorbent article with cuffs, the art has also described absorbent articles having cuffs which stand up when the absorbent article assumes an arcuate configuration when it is inserted into a wearer's undergarment for use. For example, U.S. Pat. No. 5,490,847 describes a sanitary napkin having cuffs comprising a resilient material which is said to " . . . tend to assume a vertical position when the absorbent, in use, assumes an anatomical arched configuration." While such a device may have cuffs that stand up when the absorbent article is sufficiently curved, there are many situations where the in use radius of curvature may not be small enough to cause enough curvature for the cuffs on such devices to stand up sufficiently to provide a satisfactory barrier to lateral leakage of bodily fluids, such as menses. For example, sanitary napkins can be in a substantially flat configuration when worn by women having a sufficiently large body size.

Thus, it is an object of the present invention to provide an absorbent article which takes the form of a cup as a whole, forms upwardly extending cuffs on both sides of the longitudinal centerline thereof. It is a further object of the invention to provide means such that such cuffs remain upstanding even when the absorbent article is pulled into a substantially flat-out configuration.

SUMMARY OF THE INVENTION

Disclosed herein is an absorbent article, such as a sanitary napkin, incontinent device, or the like. The absorbent article comprises a liquid pervious topsheet, a liquid impervious backsheet joined to the topsheet, and an absorbent core disposed between the topsheet and the backsheet. The absorbent article has a middle region and a pair of end regions. The absorbent article further comprises a pair of longitudinally extending cuffs disposed on the body surface of the topsheet on each side of the longitudinal centerline of the absorbent article. The cuffs are joined to at least one of the topsheet and the backsheet in a longitudinally elastically elongated state. The cuffs comprise an elastic member and a resilient member. Preferably, the elastic member comprises first and second regions which are visibly distinct from each other. The first region comprises at least two substantially planar portions and the second region comprises a plurality of raised, rib-like elements. The elastic member provides a contractive force which causes the topsheet, the core and the backsheet in each of the end regions to extend upwardly, inclinedly away from the plane of the middle region. The contractive force further causes the cuffs to extend upwardly away from the topsheet on both sides of the middle region of the absorbent article. In a particularly preferred embodiment of the present invention, at least one of the substantially planar portions of the first region of the elastic member extends in a substantially longitudinal direction and at least one other of the substantially planar portions of the first region of the elastic member is oriented at an angle with respect to the longitudinal direction, especially when the elastic member is placed in a flattened and extended condition. The resilient member cooperates with the elastic member to maintain the cuffs in an upright configuration, even when the sanitary napkin is laid substantially flat out. The resilient member resists the bending and compressive forces encountered during the normal wear cycle. Alternative embodiments of the present invention can be further provided with laterally extending flaps positioned at least in the middle region of the absorbent article and extending laterally outward from a side edge of the central absorbent body.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which reference numerals identify like elements and wherein:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united or joined together to form a coordinated entity so that they do not require separate manipulative parts like a separate holder and pad. As used herein, the term "joined" encompasses configurations whereby an element is directly secured to another element by affixing the element directly to the other element, and configurations whereby the element is indirectly secured to the other element by affixing the element to an intermediate member(s) which in turn is affixed to the other element.

General Description of the Sanitary Napkin of the Present Invention

Figure 1:
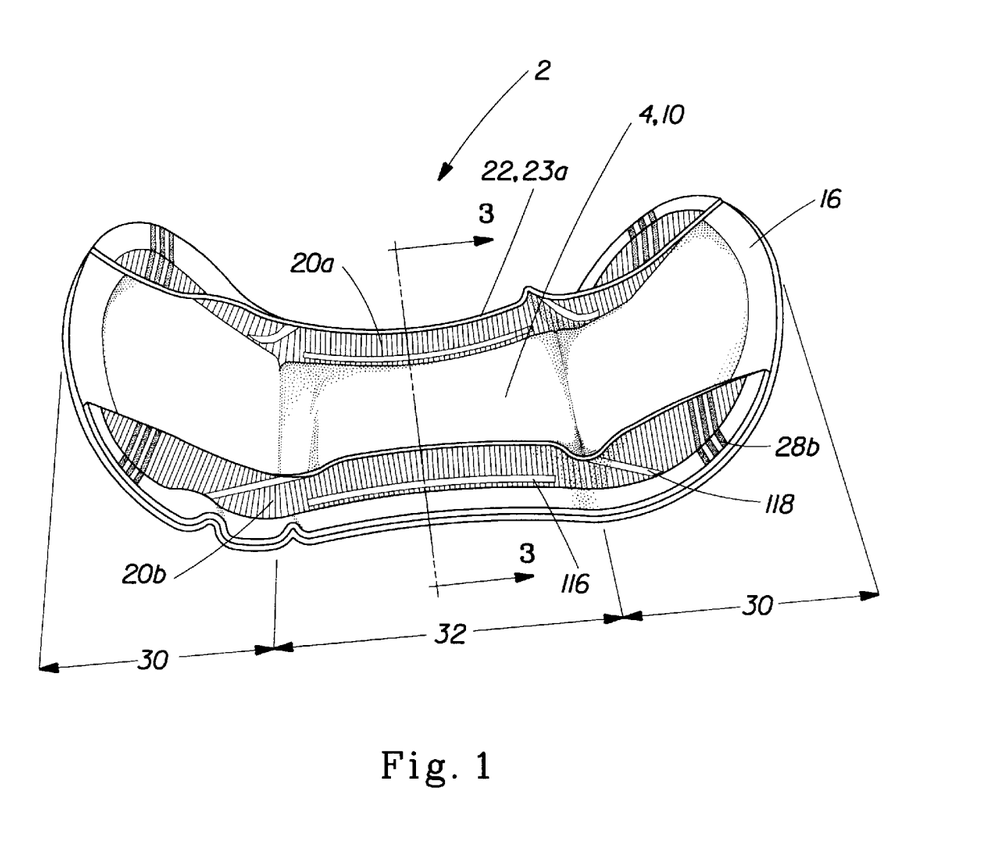
FIG. 1 is a perspective view showing a basic embodiment of a sanitary napkin according to the present invention.

A preferred embodiment of a unitary disposable absorbent article of the present invention is the sanitary napkin 2, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). As used herein, the term "pudendal" refers to the externally visible female genitalia. It should be understood, however, that the present invention is also applicable to other feminine hygiene or catamenial pads such as pantiliners, or other absorbent articles such as diapers, incontinence pads, and the like.

Figure 2:
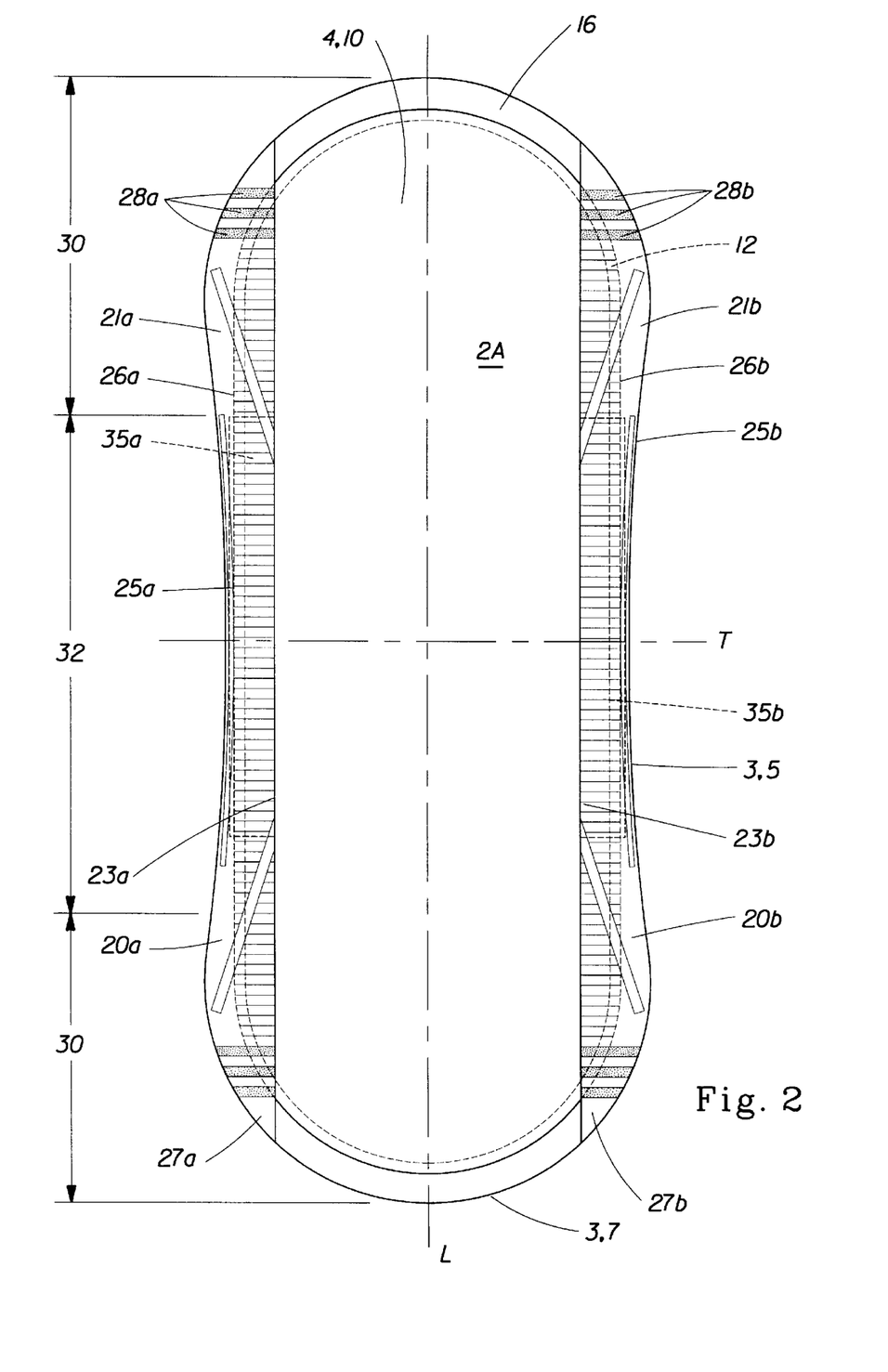
FIG. 2 is a plan view showing the sanitary napkin of FIG. 1 in its flat-out state with the cuffs elongated.
Figure 2A:
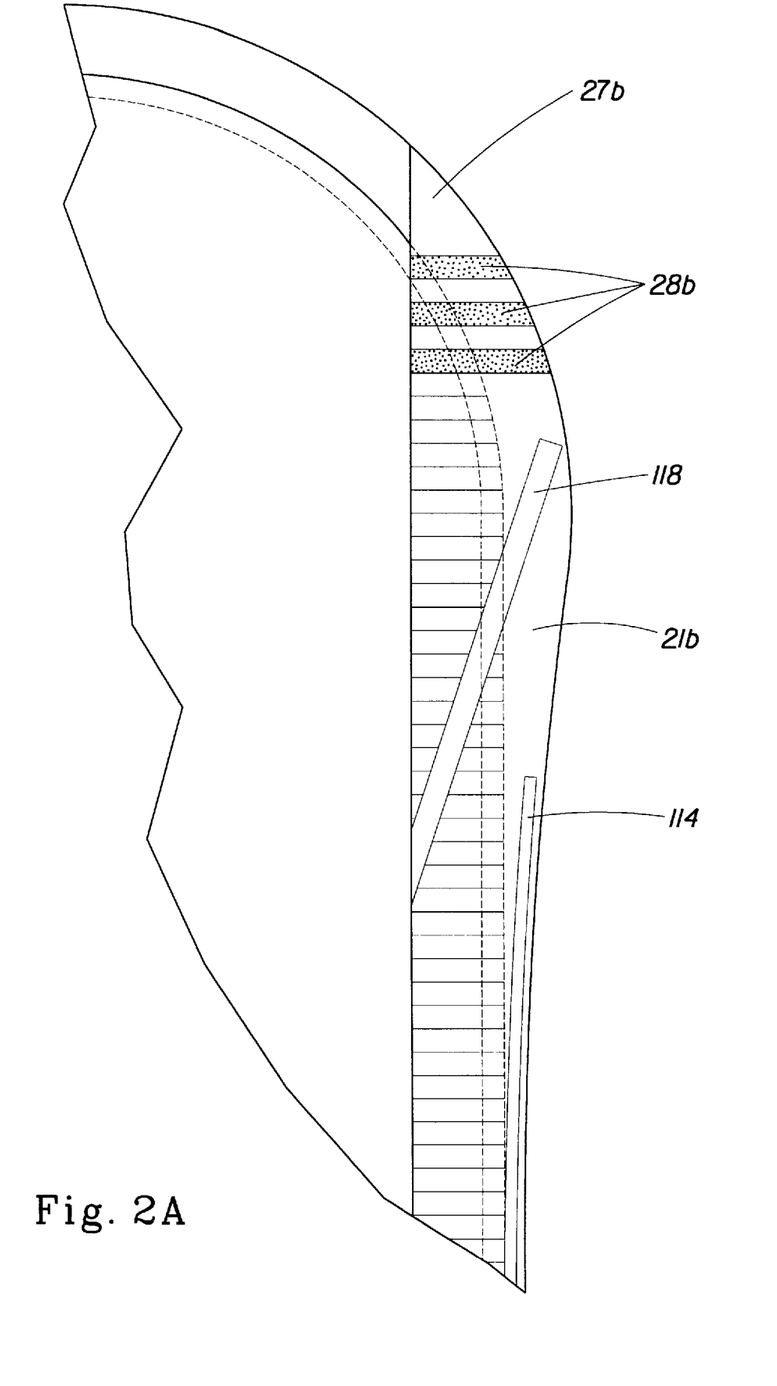
Figure 3:
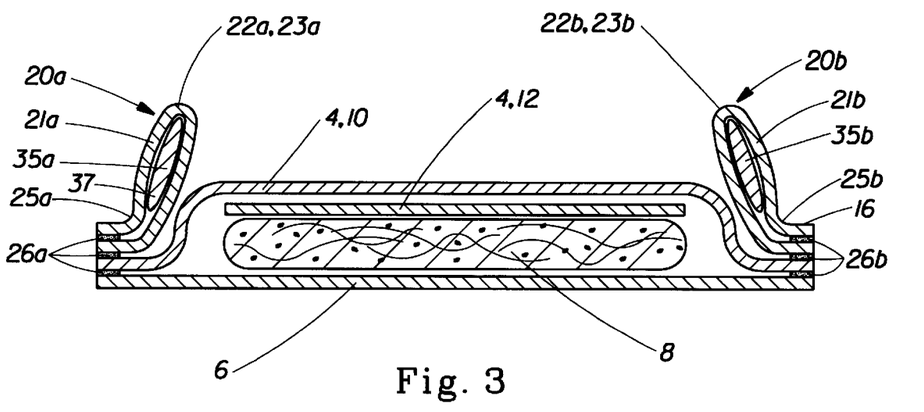
FIG. 3 is a cross sectional view taken on line 3—3 of FIG. 1.

FIGS. 1 to 3 show a sanitary napkin 2, a preferred embodiment of an absorbent article constructed in accordance with the present invention. The sanitary napkin 2, as will be understood from the following description, is not in a substantially flat form, but is cup-shaped as illustrated in FIG. 1, due to the contracting action of a SELF web as will be described below. In FIG. 2, the entire sanitary napkin 2 is shown in a substantially flat state with its cuffs elongated. The sanitary napkin 2 shown in FIGS. 1 to 3 has a liquid pervious topsheet 4, a liquid impervious backsheet 6, and an absorbent core 8 positioned between the topsheet 4 and the backsheet 6. The sanitary napkin 2 further comprises longitudinally extending cuffs 20, the cuffs 20 comprising an elastic member 21 and a resilient member 35. As will be described below, the elastic member 21 causes the distal edge 23 of the cuffs 20 to extend upward above the plane of the topsheet 4 and provide the sanitary napkin 2 of the present invention with a cup-like configuration. The resilient member 35 cooperates with the elastic member 21 to help maintain the cuffs 20 in an upright configuration even when the sanitary napkin 2 is pulled substantially flat out. The resilient member 35 further provides resistance to the bending and compressive forces that are encountered during normal wear.

The sanitary napkin 2 has two surfaces, a body-contacting surface or "body surface" 2A and a garment surface 2B. In a similar manner, the body surface of other components of the sanitary napkin 2 having a body surface will be referred to using the reference number for the component followed by the letter A and any reference to the garment surface of a component will use the reference number for the component followed by the letter B. The sanitary napkin 2 is shown in FIG. 2 as viewed from its body surface. The body surface 2A is intended to be worn adjacent to the body of the wearer. At least a portion of the body surface 2A comprises the topsheet 4. The garment surface 2B is on the opposite side of the sanitary napkin 2 and is intended to be placed adjacent to the wearer's undergarments when the sanitary napkin 2 is worn. At least a portion of the garment surface 2B comprises the backsheet 6. The sanitary napkin 2 has two centerlines, a longitudinal centerline L and a transverse centerline T. The term "longitudinal", as used herein, refers to a line, axis or direction in the plane of the sanitary napkin 2 that is generally aligned with (e.g., approximately parallel to) a vertical plane which bisects a standing wearer into left and right body halves when the sanitary napkin 2 is worn. The terms "transverse" or "lateral" as used herein, are interchangeable, and refer to a line, axis or direction which lies within the plane of the sanitary napkin 2 that is generally perpendicular to the longitudinal direction. FIG. 2 also shows that the sanitary napkin 2 has a periphery 3 which is defined by the outer edges of the sanitary napkin 2 in which the longitudinal edges are designated 5 and the end edges are designated 7. As can also be seen in FIGS. 1 and 2, the sanitary napkin 2 comprises longitudinally opposite end regions 30 and a central region 32.

The Topsheet

The topsheet 4 should permit bodily discharges from the wearer to rapidly penetrate its thickness for absorption by the absorbent core 8, and should not cause excessive discomfort to the wearer when it is in contact with the wearer's skin. The topsheet 4 forms at least a portion of the body surface 2A of the sanitary napkin 2.

The topsheet 4 can be formed from materials, such as woven or nonwoven fabrics comprising natural or synthetic fibers; apertured thermoplastic films; porous foams; reticulated foams; reticulated thermoplastic films; and thermoplastic scrims. In the preferred embodiment shown in FIGS. 1 to 3, the topsheet 4 comprises a composite topsheet comprising a primary topsheet layer 10 and a secondary topsheet layer 12 (seen most clearly in FIG. 3). The primary topsheet layer 10 and the secondary topsheet layer 12 are joined to form composite topsheet 4 using means familiar to those skilled in the art such as adhesive bonding, ultrasonic welding, or thermal bonding which is carried out in a multiplicity of discrete areas. An exemplary means for joining the primary topsheet layer 10 to the secondary topsheet layer 12 to form composite topsheet 4 comprises the use of fusion bonds as is more fully described in U.S. patent application Ser. No. 07/810,774, filed Dec. 17, 1991 in the names of Cree, et al and published as PCT Application Ser. No. WO 93/11725 on Jun. 24, 1993, the disclosure of which is incorporated herein by reference. In a preferred embodiment, the secondary topsheet layer 12 may be joined to the primary topsheet layer 10 to form composite topsheet 4 by several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. The disclosure of each of these patents is incorporated herein by reference.

As can be seen in FIG. 2, the primary topsheet layer 10 preferably has a substantially rectangular configuration. A portion of the primary topsheet layer 10 extends convexly arcuately outward to form a portion of the end edges 7 of the sanitary napkin 2.

A suitable primary topsheet layer 10 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred primary topsheet layer 10 comprises an apertured formed film. Apertured formed films are preferred for the primary topsheet layer 10 because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, which issued to Thompson on Dec. 30, 1975; U.S. Pat. No. 4,324,246, which issued to Mullane, et al. on Apr. 13, 1982; U.S. Pat. No. 4,342,314, which issued to Radel. et al. on Aug. 3, 1982; U.S. Pat. No. 4,463,045, which issued to Ahr et al. on Jul. 31, 1984; and U.S. Pat. No. 5,006,394, which issued to Baird on Apr. 9, 1991. The disclosure of each of these patents is incorporated herein by reference. The preferred primary topsheet layer 10 for the present invention is the formed film described in one or more of the above patents and marketed on sanitary napkins by The Procter & Gamble Company of Cincinnati, Ohio as "DRI-WEAVE".

In a preferred embodiment of the present invention, the body surface 10A of the formed film primary topsheet layer 10 is hydrophilic so as to help liquid to transfer through the composite topsheet 4 faster than if the body surface was not hydrophilic so as to diminish the likelihood that menstrual fluid will flow off the primary topsheet layer 10 rather than flowing into and being absorbed by the absorbent core. In a preferred embodiment, surfactant is incorporated into the polymeric materials of the formed film primary topsheet layer 10 such as is described in U.S. patent application Ser. No. 07/794,745, filed on Nov. 19, 1991 by Aziz, et al., and published as PCT Application Ser. No. WO 93/09741 on May 27, 1993 the disclosure of which is incorporated herein by reference. Alternatively, the body surface of the primary topsheet layer 10 can be made hydrophilic by treating it with a surfactant such as is described in U.S. Pat. No. 4,950,264, issued to Osborn, III on Aug. 21, 1990, the disclosure of which is incorporated herein by reference.

The secondary topsheet layer 12 lies between the primary topsheet layer 10 and the absorbent core 8 and is joined to the inner surface of the primary topsheet layer 10 to form composite topsheet 4 as described above. The secondary topsheet layer 12 of composite topsheet 4 is similar in shape to the primary topsheet layer 10, but preferably with smaller longitudinal and transverse dimensions than the longitudinal and transverse dimensions of the primary topsheet layer 10. That is, the periphery of the primary topsheet layer 10 is larger than the periphery of the secondary topsheet layer 12 of composite topsheet 4. The secondary topsheet layer 12 of composite topsheet 4 disperses bodily fluids, which have passed through the primary topsheet layer 10, mainly in the longitudinal direction, such that the absorbent core 8 is more filly utilized.

The secondary topsheet layer 12 of composite topsheet 4 may serve several functions including improving wicking of exudates over and into the absorbent core 8. There are several reasons why the improved wicking of exudates is important, including providing a more even distribution of the exudates throughout the absorbent core and allowing the sanitary napkin 2 to be made relatively thin. (The wicking referred to herein may encompass the transportation of liquids in one, two or all directions (i.e., in the x-y plane and/or in the z-direction.) The secondary topsheet layer 12 of composite topsheet 4 may comprise several different materials including nonwoven or woven webs of synthetic fibers including polyester, polypropylene, or polyethylene; natural fibers including cotton or cellulose; blends of synthetic and natural fibers; or any equivalent materials or combinations of materials. Examples of sanitary napkins having a secondary topsheet layer 12 of composite topsheet 4 are more fully described in the above-referenced U.S. Pat. No. 4,950,264 and the above-referenced Cree application. The disclosure of each of these publications is incorporated herein by reference. Preferably, the secondary topsheet layer 12 of composite topsheet 4 is formed from a natural or synthetic nonwoven fabric. A particularly preferred nonwoven material for the secondary topsheet layer 12 comprises an air laid tissue having a basis weight of about 35 grams per square meter (gsm). A suitable material is available from Merfin Hygiene Products Ltd., Delta, BC, Canada. Alternative nonwoven materials suitable for forming the secondary topsheet layer 12 of composite topsheet 4 include a nonwoven fabric of spunbonded polypropylene fibers available from the Fiberweb Corporation of Simpsonville, S.C. under the tradename CELESTRA and a nonwoven fabric formed of bicomponent fibers which have a polyethylene sheath and a polyurethane core, which is available from the Havix Company, of Japan, as S2416.

The Backsheet

The backsheet 6 is intended to prevent bodily fluids absorbed by the absorbent core 8 from flowing out of the sanitary napkin and soiling the wearer and/or the wearer's clothing. Preferably, the backsheet 6 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 6 prevents the exudates absorbed and contained in the absorbent core 8 from wetting articles which contact the sanitary napkin 2 such as pants, pajamas and undergarments. The backsheet 6 may, thus, comprise a woven or nonwoven material, polymeric films such as thermoplastic films of polyethylene or polypropylene, or composite materials such as a film-coated nonwoven material. Preferably, backsheet 6 can comprise a flexible liquid impervious thermoplastic film such as a polyolefinic film. Particularly preferred films for forming the backsheet 6 include a low density polyethylene film having a caliper of from about 0.01 mm (0.4 mils) to about 0.05 mm (2.0 mils), preferably about 0.025 mm (1.0 mil). Such a polyethylene film is sold by the Ethyl Corp., Visqueen Division, of Terre Haute, Ind., as Model XP-39385 and by the Clopay Corp. of Cincinnati, Ohio as SOFFLEX 1401.

As shown most clearly in FIG. 2, the backsheet 6 has a shape and dimensions which are substantially the same as those of the primary topsheet layer 10 of composite topsheet 4. The primary topsheet layer 10 of composite topsheet 4 and the backsheet 6 are bonded uninterruptedly throughout their periphery (i. e., throughout the periphery 3 of sanitary napkin 2). This area of peripheral bonding 16 is shown most clearly in FIG. 2. That portion of the area of peripheral bonding 16 that lies adjacent the longitudinal edges of the sanitary napkin 2 in central region 32 is known as the arcuate seal 29. Means for joining the primary topsheet layer 10 and the backsheet 6 in the area of peripheral bonding 16 can comprise any sealing means known to the art such as ultrasonic welding, adhesive bonding, or other means known to the art. Preferably, the primary topsheet layer 10 and the backsheet 6 are joined in the area of peripheral bonding 16 by at least one seal formed by the application of pressure, with or without heat, commonly referred to as a crimp seal. Alternatively, the primary topsheet layer 10 and the backsheet 6 may be joined together in any other suitable manner, such as bonding with an adhesive.

The Absorbent Core

The absorbent core 8, which is disposed between the topsheet 4 and the backsheet 6, absorbs and retains bodily fluids that have penetrated the topsheet 4 after discharge by a wearer. The absorbent core 8 may be any absorbent means which is capable of absorbing or retaining bodily liquids (e.g., menses and/or urine). The absorbent core 8 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinence pads, pantiliners, regular sanitary napkins, or overnight sanitary napkins. Exemplary absorbent structures suitable for use as the absorbent core of the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; European Patent Application No. 0 198 683, The Procter & Gamble Company, published Oct. 22, 1986 in the name of Duenk, et al.; and U.S. Pat. No. 5,009,653 issued to Osborn, III, on Apr. 23, 1991. The disclosure of each of these patents is incorporated herein by reference.

The longitudinal and transverse dimensions of core 8, as it is shown in FIG. 2, are preferably smaller than the longitudinal and transverse dimensions of the primary topsheet layer 10 and the backsheet 6. Preferably, core 8 lies within the region defined by the areas of peripheral bonding 16 between the composite topsheet 4 and the backsheet 6. More preferably, the secondary topsheet layer 12 of composite topsheet 4 is disposed between the core 8 and the primary topsheet layer 10 and the longitudinal and transverse dimensions of the secondary topsheet layer 12 of composite topsheet 4 are somewhat larger than or substantially equal to the longitudinal and transverse dimensions of core 8.

The top surface (i. e., the surface closest to the topsheet 4) of the core 8 is joined to the lower surface of the secondary topsheet layer 12 of composite topsheet 4, while the lower surface of the core 8 is joined to the inner surface or top surface of the backsheet 6. The core 8 may be joined to the secondary topsheet layer 12 of composite topsheet 4 and to the backsheet 6 using means known to those skilled in the art (not shown) such as by bonding using a suitable adhesive. Preferably the core 8 is joined to the secondary topsheet layer 12 and to the backsheet 6 using an open pattern network of filaments comprises several lines of adhesive filaments swirled into a spiral pattern as discussed above. Adhesives which have been found to be satisfactory are manufactured by H. B. Fuller Company of St. Paul, Minn. under the designation HL-1258 or H-2031. Alternatively, the core 8 may be joined to the secondary topsheet layer 12 of composite topsheet 4 and/or the backsheet 6 in any other suitable manner, such as by ultrasonic welding or thermal bonding.

The Fastening Adhesive

In use, the sanitary napkin 2 can be held in place by any support means or attachment means (not shown) well-known for such purposes. Preferably, the sanitary napkin is placed in the user's undergarment or panty and secured thereto by a fastener such as an adhesive. The adhesive provides a means for securing the sanitary napkin in the crotch portion of the panty. Thus, a portion or all of the garment surface of the backsheet 6 may be coated with adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio and Instant Lock 34-2823 manufactured by the National Starch and Chemical Company of Bridgewater, N.J. Suitable adhesive fasteners are also described in U.S. Pat. No. 4,917,697 issued to Osborn III, et al. on Apr. 17, 1990, the disclosure of which is incorporated herein by reference. Before the sanitary napkin is placed in use, the pressure-sensitive adhesive is typically covered with a removable release liner in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. Preferably, a release liner is used which also serves as an individual package for the sanitary napkin 2. Suitable release liners that also serve as a package for an individual sanitary napkin are described in U.S. Pat. No. 4,556,146, issued to Swanson, et al., the disclosure of which is incorporated herein by reference. The sanitary napkin of the present invention is used by removing the release liner and thereafter placing the sanitary napkin in a panty so that the adhesive contacts the panty. The adhesive maintains the sanitary napkin in its position within the panty during use.

The Cuffs

With further reference to FIGS. 1 to 3, the preferred embodiment of the sanitary napkin 2 of the present invention further comprises a pair of cuffs 20a and 20b. In a similar manner, pairs of elements that are disposed on opposite sides of the sanitary napkin 2 will be referred to using the reference number for the element followed either by the lower case letter a or the letter b. Each of the cuffs 20a and 20b comprises an elastic member 21a, 21b and a resilient member 35a, 35b (shown most clearly in FIG. 3). Each cuff 20a, 20b is disposed on the body surface of the topsheet 4 in an elongated state, and is joined to the topsheet 4 in that elongated state as is described below.

As will be easily understood by reference to FIG. 3, the elastic member 21 is first folded back along longitudinally extending lines 22 to enclose the resilient member 35 and to form distal edge 23 and opposed proximal edge 25. That is, the elastic member 21 is C-folded about the resilient member 35. While the resilient member 35 can extend the entire length of the cuff 20, it is preferably positioned only in central region 32. If desired, a small portion of the longitudinal length of the resilient member 35 may be joined to the elastic member 21 using means known to the art to help stabilize the resilient member 35 during subsequent assembly operations. Otherwise, the resilient member 35 should "float" freely within the elastic member 21 so it does not interfere with the lifting action provided by the elastic member (discussed below).

The folded cuffs 20 are elongated to a predetermined length and disposed on topsheet 4, one cuff 20 on each side of centerline L, with the distal edges 23a and 23b directed inwardly toward and substantially parallel with longitudinal centerline L and the proximal edges 25a and 25b lying juxtaposed with the longitudinal edges 5 of sanitary napkin 2.

Each of the cuffs 20a and 20b has the respective layers of the elastic member 21a, 21b joined together adjacent the proximal edges 25a and 25b thereof, and is further bonded, using first bonding means 26a and 26b, to the primary topsheet layer 10 of the topsheet 4, throughout that portion of each cuff 20a and 20b that lies within the area of peripheral bonding 16 lying along the longitudinal edges 5. Preferably, such first bonding means 26 comprises the application of pressure, with or without heat, commonly referred to as a crimping, although other means, such as, adhesive bonding or ultrasonic bonding are also suitable.

The spacing between resilient member proximal edge 37 and first bonding means 26 should be minimized when the cuff 20 is joined to the primary topsheet layer 10. If this spacing becomes too large, the resilient member 35 ceases to effectively resist bending about proximal edge 25 of cuff 20. Stated another way, if the spacing is too large, there is enough of the material comprising the elastic member 21 between the first bonding means 26 and resilient member proximal edge 37 to act as a hinge which facilitates such bending. Preferably, such spacing should be less than about 2.5 millimeters (0.1 inch). More preferably, such spacing should be less than about 2 millimeters (0.8 inch). Still more preferably, the resilient member 35 should just contact the first bonding means 26 (i. e., the spacing is 0 mm or 0 inches).

A portion of each cuff 20a and 20b is then bonded to the underlying portion of the cuff 20 with second bonding means 27a and 27b. Second bonding means 27 also bonds the cuffs 20 to the primary topsheet layer 10 in that portion of the peripheral bonding area 16 adjacent the end edges 7. Preferably, such second bonding means 27 are same as those used to comprise first bonding means 26. Optimally, first bonding means 26 and second bonding means 27 combine such that the area of peripheral bonding 16, which joins the topsheet 4 to the backsheet 6, is formed at the same time the cuffs 20 are bonded to the topsheet 4. Alternatively, the elastic members 21a, 21b can be C-folded about the resilient members 35a, 35b as described above, disposed on the topsheet 4 in an elongated configuration, and bonded to the topsheet in a single crimping step that combines the effects of first bonding means 26 and second bonding means 27 while forming the area of peripheral bonding 16.

The portion of the cuffs 20 lying in end regions 30 are further joined to underlying structure using tertiary bonding means 28 at a plurality of spaced apart sites. Importantly, at least a portion of the plurality of sites for tertiary bonds 28a and 28b overlies core 8 to prevent the corners of sanitary napkin 2 from bending in toward the longitudinal centerline L. The tertiary bonds 28a and 28b disrupt the "elastic-like" structure of the cuffs 20a and 20b (discussed below) so there is no contractive force in end regions 30 to cause the corners to bend in. Further, cuffs 20a and 20b are locally joined to the relatively stiff core 8 via the primary topsheet layer 10, effectively transmitting the contracting action of cuffs 20a and 20b to core 8. This transmission of forces further resists the undesirable local bending in the four corners of the sanitary napkin 2. Consequently, the topsheet 4, backsheet 6 and core 8 are caused to extend inclinedly upward away from the plane of the central region 32 in each of the end regions 30, forming the desired cup-like configuration. For example, three sites of tertiary bonds 28a and 28b are shown in FIGS. 1 and 2. As can be seen in FIG. 2, one of such bonds 28a and one bond 28b do not overlie core 8. While the remaining two bonds 28a and 28b do overlie core 8. Preferably tertiary bonds 28 comprise dynamic mechanical bonds as described in US Pat. No. 4,854,984, issued to Ball, et al. on Aug. 8, 1989. Alternatively, other suitable methods, such as, thermal bonding, crimping, or ultrasonic welding may be employed as tertiary bonding means 28 to join the cuffs 20a and 20b to underlying structure in the end regions 30.

As has been mentioned above, cuffs 20a and 20b are bonded to the topsheet 4 at a plurality of sites for tertiary bonds 28a and 28b in addition to the first bonding means 26a and 26b and second bonding means 27a and 27b which join the cuffs 20a and 20b to the topsheet in the area of peripheral bonding 16. Since, in the preferred embodiment of the present invention shown in FIGS. 1–3, the contractive force of the cuffs 20a and 20b is generated mainly by the unformed portions 38 of the SELF web (discussed below), it is important that the tertiary bonds 28a and 28b be positioned such that the bond area for tertiary bonds 28a, 28b includes unformed portions 38. Also, the bond area for tertiary bonds 28a and 28b should preferably be minimized to minimize the creation of occluding areas that can cause wearer discomfort. One way to minimize the bond area is to provide tertiary bonds 28a and 28b at a plurality sites, each having a relatively small area, which are disposed at spaced apart locations instead of providing one bond 28a and one bond 28b each having a relatively large area at each end of each of the cuffs 20. Such a multi-site configuration for tertiary bonds 28a and 28b is shown in FIGS. 1 and 2.

As noted above, cuffs 20a and 20b are disposed on the topsheet 4 in an elongated state, and are bonded thereto by bonding means 26a and 26b, 27a and 27b, and 28a and 28b. When the force that has maintained the cuffs 20a and 20b in an elongated condition is released, the unbonded portions of the elastic members 21a, 21b contract, and thus, the cuffs 20a and 20b, at least partially, return to their original lengths. This contracting action generated in the cuffs 20a and 20b, causes the topsheet 4, the backsheet 6 and the core 8 to be displaced so that end regions 30 lie above central region 32 as is clearly illustrated in FIG. 1. Thus, the sanitary napkin 2 is brought into the shape of a cup as a whole. In addition, in central region 32, the distal edge 23 of each of the cuffs 20a and 20b extends upward and away from the plane of the topsheet 4 forming a barrier which impedes the lateral flow of bodily fluids with a resulting reduction in leakage along the longitudinal edges 5 of the sanitary napkin 2. The degree of elongation imparted to the cuffs 20a and 20b when they are disposed on the topsheet 4 and bonded thereto depends on the overall configuration and dimensions of the sanitary napkin 2 and on the specific material used for the elastic member 21. For the embodiment of the present invention shown in FIGS. 1 to 3 elongation should be between about 110% to about 160%, preferably, between about 115% and about 145%, and, more preferably, about 125% of the length of an unelongated cuff 20.

The Elastic Member

In the sanitary napkin 2 of the present invention, the elastic members 21a, 21b can comprise any material that provides sufficient contractive force to cause the sanitary napkin to assume the cup-like configuration shown in FIG. 1 and to lift the cuffs 20 above the body surface 4A of the composite topsheet 4. Preferably, such material is also soft and comfortable where it contacts a wearer's body. For example, the elastic member 21 can comprise an elastomeric film material such as is available from Exxon Chemical Corp. Bay City, Tex. as EXX500.

Preferably, however, the elastic members 21a, 21b comprise a web formed at least partially in a non-planar configuration to provide a "Structural Elastic-Like Film" (SELF) web. A particularly preferred embodiment of a SELF web is a web comprising a thermoplastic film, especially, a polyolefinic film such as a polyethylene film, which includes, in a suitable combination, formed portions formed in a non-planar configuration as described below, and unformed portions retained in a substantially planar configuration. SELF webs are described in detail in commonly assigned U.S. Pat. No. 5,518,801, issued to Chappell, et, al., on May 21, 1996. The disclosure of which is incorporated herein by reference. When the elastic members 21a and 21b are produced from a web including formed portions and the longitudinally extending unformed portions as are described below, the contracting action of the cuffs 20a and 20b is generated mainly by the restoring force of the unformed portions, as will be clearly understood from the following description.

As used herein, the term "formed" refers to the creation of a desired structure or geometry upon a web of material that will substantially retain the desired structure or geometry when it is not subjected to any externally applied elongation or forces. Methods suitable for forming a web of material such that the web is transformed into a SELF web include, but are not limited to, embossing by mating plates or rolls, thermoforming, high pressure hydraulic forming, and casting.

Figure 4:
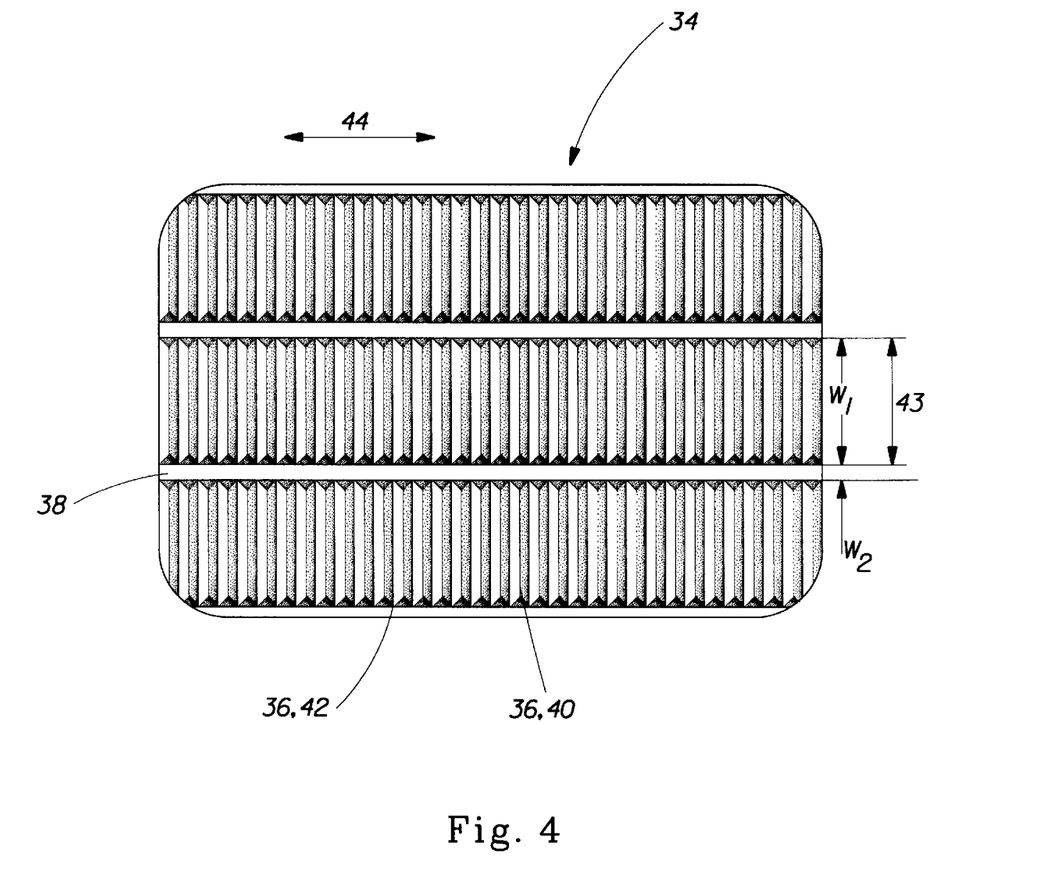
FIG. 4 is a plan view showing a portion of the structural elastic-like film (SELF) web used to form the cuffs of the sanitary napkin illustrated in FIG. 1.
Figure 5:
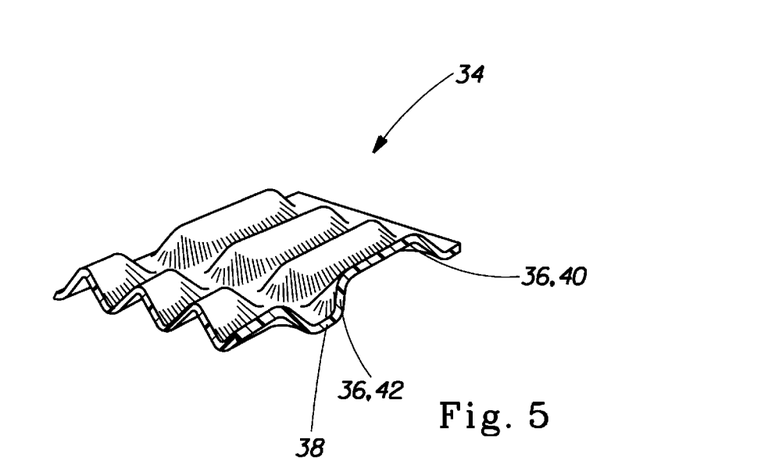
FIG. 5 is an enlarged perspective view showing part of the SELF web illustrated in FIG. 4.

FIGS. 4 and 5 show a web 34 in the form of a SELF web that is suitable for cuffs 20a and 20b. This web 34 comprises formed portions 36 formed in a non-planar configuration as described below, and unformed portions 38 retained in a substantially planar configuration. As is seen clearly in FIG. 4, the formed portions 36 and the unformed portions 38 are arranged alternately in a side-by-side relationship in the transverse direction (shown by arrows 43 in FIG. 4), and extend uninterruptedly in the longitudinal direction (shown by arrows 44 in FIG. 4). As will be understood by reference to FIGS. 4 and 5, the formed portion 36 includes a primary formed portion 40, and secondary formed portions 42 located on both sides in the transverse direction. As seen most clearly in FIG. 5, the primary formed portion 40 takes a substantially uniform, nearly sinusoidal form in its longitudinal cross section, and takes a substantially horizontally extending linear form in its transverse cross section. The secondary formed portion 42 is a region of transition from the primary formed portion 40 and the unformed portion 38.

The proportion of the unformed portions 38 in the web 34 is between about 1% and about 30%, preferably between about 3% and about 20%, more preferably between about 5% and about 12%, when calculated as the ratio of the respective areas (assuming that the web 34 is in a non-elongated state and the area occupied by formed portions 36, including the primary formed portions 40 and the secondary formed portions 42, is projected to the plane of unformed portion 38). This is illustrated by the projection shown in the non-elongated plan view of FIG. 4. In other words, the proportion of the formed portions 36 (including the primary formed portions 40 and the secondary formed portions 42) in the web 34 is between about 70% and about 99%, preferably between about 80% and about 97%, and more preferably between about 88% and about 95%. If the proportion of the unformed portions 38 in the web 34 is too high, the force required to elongate the cuffs 20a and 20b tends to become too high. If the proportion of the unformed portions 38 in the web 34 is too low, the contractive force of the cuffs 20a and 20b is minimal, making it difficult to shape the sanitary napkin 2 into the desired cup-like configuration.

Furthermore, since the formed portions 36 are in a non-planar configuration, they touch the skin of the sanitary napkin 2 wearer only locally at a plurality of small spaced apart regions. Consequently, the discomfort they may cause to the wearer is limited because the sanitary napkin 2 can "breathe". In contrast, if the proportion of the unformed portions 38 is too high and the unformed portions 38 are the main source of contact between the sanitary napkin 2 and the wearer's skin, the unformed portions 38 in a planar configuration touch the wearer's skin uninterruptedly over a relatively large area. Thus, they may cause discomfort to the wearer. Generally, as can be seen in FIG. 4, the width $W_1$ of the formed portion 36 is 0.25 to 50.80 mm (0.01 to 2.00 inches), preferably, 3.18 to 25.40 mm (0.13 to 1.00 inch), while the width $W_2$ of the unformed portion 38 is 0.25 to 12.70 mm (0.01 to 0.50 inch), preferably, 0.76 to 6.35 mm (0.03 to 0.25 inch).

The web 34 shown in FIGS. 4 and 5 exhibits desirable "elastic-like" behavior when the cuffs 20a and 20b are stretched in the longitudinal direction indicated by arrows 44. When a longitudinal stretching force is exerted on the web 34, its cross sectional configuration is geometrically changed, with the amplitude of the formed portions 36 being gradually decreased. Upon a further elongation, the web 34 becomes substantially planar. During the change of the formed portions 36 from the state illustrated in FIG. 5, to the partially stretched state, and, finally, to the flat out state, the force contribution of the formed portions 36 to the total force resisting the elongation is markedly low. The unformed portions 38, on the other hand, are elongated by molecular-level deformation of the constituent material itself, and the resistive force of the web 34 to elongation is mainly provided by the unformed portions 38. In other words, in the range where the elongation of the formed portions 36 is attributable to geometric deformation, rather than to the molecular-level deformation of the material itself, the contracting action of the web 34 upon release of a stretching force exerted on the web 34 results mainly from the contracting action due to molecular-level deformation of the unformed portions 38.

Figure 6:
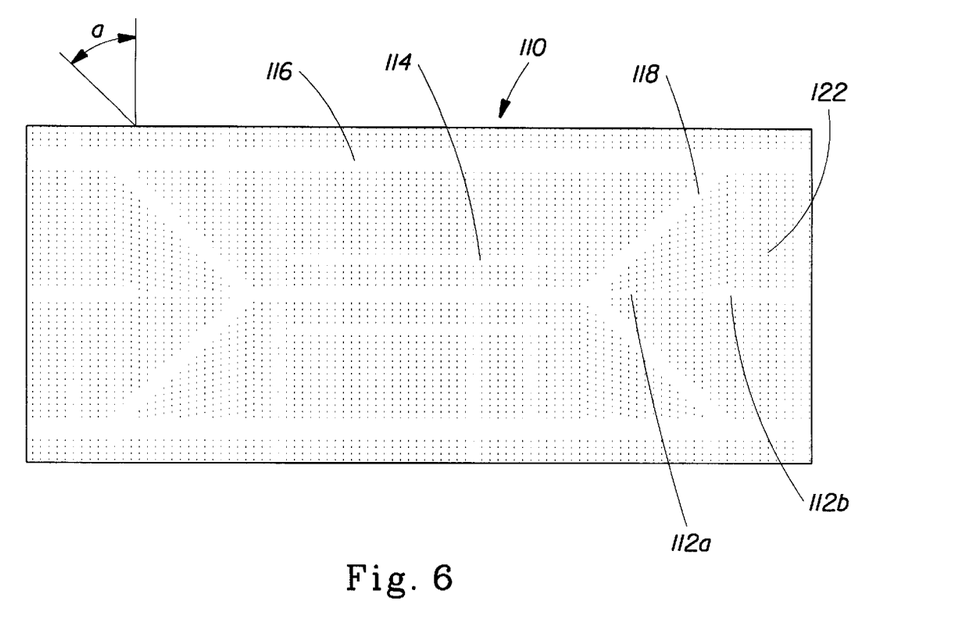
FIG. 6 is a plan view, similar to FIG. 4, showing a preferred embodiment of a SELF web.
Figure 7:
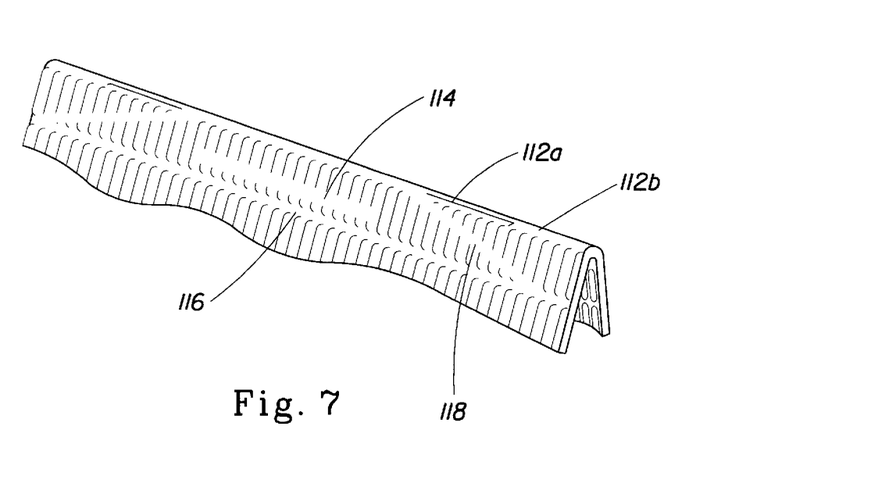
FIG. 7 is a perspective view of the SELF web illustrated in FIG. 6 which has been folded back along the unformed portion.

A particularly preferred pattern relationship between the formed portions and the unformed portions of a SELF web is shown in plan view in FIG. 6 and in perspective view in FIG. 7. FIGS. 6 and 7 show a SELF web 110 that not only comprises laterally oriented formed portions 122 and longitudinally oriented unformed portions (fold line 112, hinge 114, and longitudinal band 116) but also a diagonally oriented angled band 118. As is shown most clearly in FIG. 6, angled band 118 is disposed at an angle a with respect to a line parallel to the formed portions 122. As can also be seen in FIGS. 6 and 7, the web is symmetrical about the fold line 112.

As can be seen in FIG. 2, such a web is suitable for use as the elastic member 21 of a cuff 20 for sanitary napkin 2. When web 110 is folded about fold line 112 as is described above and shown in FIG. 7, the distal edge 23 of cuff 20 is formed. The cuff 20 is then extended, disposed on, and joined to the body surface 4A of composite topsheet 4 as described above.

Angled band 118 provides a cuff, such as cuff 20 shown in FIG. 2, with a bi-directional force vector that causes cuff 20 to rotate about hinge 114 in a direction outward from centerline L with a resulting lifting of the distal edge 23 of cuff 20 in the vertical or "z" direction with respect to the body surface 4A of composite topsheet 4 even when the sanitary napkin 2 is in a substantially flat-out configuration. The angle a (shown in FIG. 12) is particularly important with respect to the degree of lifting provided by angled band 118. For example, if angle a is about 30 degrees (i.e. about 60 degrees with respect to the longitudinal centerline L), there is insufficient lifting force to cause the distal edge 23 to be displaced upward when the sanitary napkin 2 is in a substantially flat-out configuration. (Such a substantially flat-out configuration is encountered during sanitary napkin use by medium to large size wearers.) Preferably, the angle a is between about 45 degrees and about 75 degrees (i.e. between about 15 degrees and about 45 degrees with respect to the longitudinal centerline L). In a particularly preferred embodiment, the angle a is about 60 degrees (i.e. about 30 degrees with respect to the longitudinal centerline L).

The spacing between the fold line 112 and the hinge 114 is also important. Formed portions 122 create laterally oriented pleats which resist bending. If the spacing between fold line 112 and hinge 114 is too large there is insufficient bending resistance against externally applied forces such as those encountered during the wear cycle and the cuff 20 would tend to fold over and inward during use. It has been found that a spacing between fold line 112 and hinge 114 of between about 0.3 inches (8 millimeters) and about 0.6 inches (16 millimeters) is satisfactory. Particularly preferred is a spacing of about 0.5 inches (12 millimeters) between the fold line 112 and the hinge 114.

Figure 8:
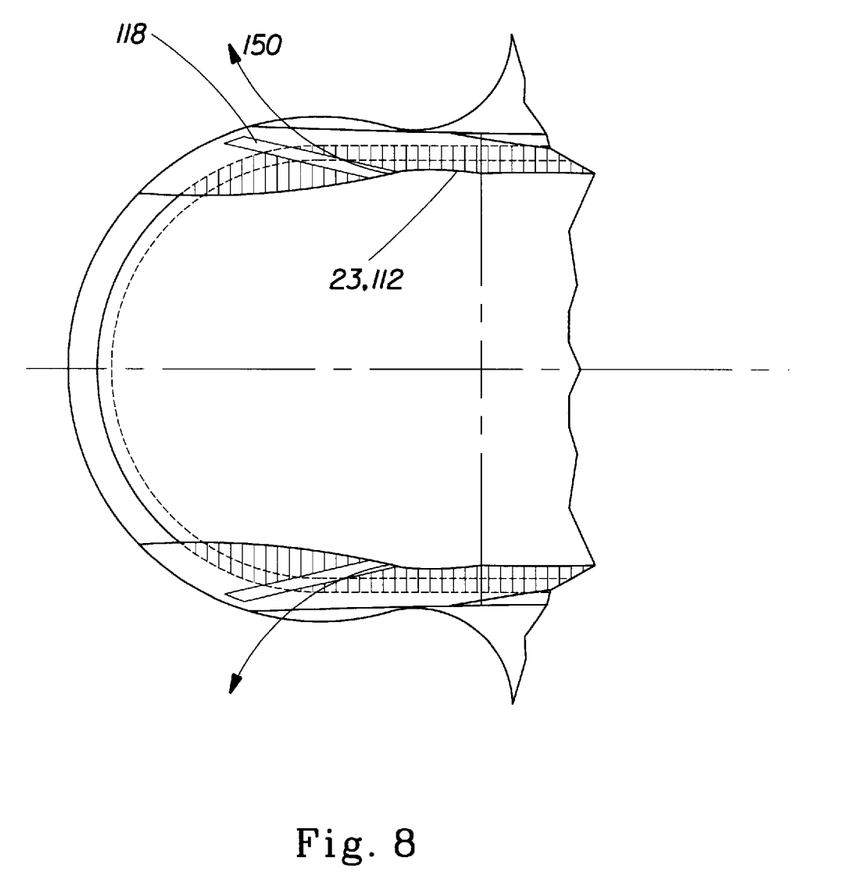
FIG. 8 is a diagrammatic representation of how a line of contractive force is carried through the cuff of the sanitary napkin illustrated in FIG. 2.

It is also important that angled band 118 intercept both the fold line 112 and the longitudinal band 116. This intersection of bands causes the line of tension that causes the distal edge 23 of cuffs 20 to be elevated above the body surface 4A of composite topsheet 4 to be carried through the fold line 112 to the angled band 118 for transfer to underlying layers of the sanitary napkin 2 in end regions 30. This is shown most clearly in FIG. 8 which shows how the line of tension 150 is directed along the various unformed portions of the preferred SELF web.

As can also be seen most clearly in FIG. 6, fold line 112 comprises two portions 112a and 112b. While both portions are unformed, portion 112a is substantially narrower than portion 112b. The narrower unformed portion 112a helps insure that the line of tension is carried along angled band 118 rather than continuing along the distal edge 23 (i.e. fold line 112) since portion 112a will stretch more readily in response to an applied force. However, it is necessary that fold line 112 be continuous to enable web 110 to be folded about resilient member 35 to form cuff 20 and distal edge 23 in a reliable manner.

Web materials suitable for conversion into a SELF web such as those shown in FIGS. 4–7, are preferably thermoplastic films, particularly polyolefin films, including linear low density polyethylene, low density polyethylene, ultra low density polyethylene, high density polyethylene, polypropylene, or blends of these. Additional suitable web materials include polyester, polyurethanes, compostable or biodegradable polymers, heat shrink polymers, thermoplastic elastomers, metallocene catalyst-based polymers (e.g., INSITE available from Dow Chemical Company Midland, Mich. and Exxact available from Exxon Chemical Corp. Bay City, Tex.), and breathable polymeric films. Also suitable are webs comprising synthetic woven materials, synthetic knit materials, nonwoven materials, apertured films, macroscopically expanded three-dimensional formed films, absorbent or fibrous materials, foams, filled compositions, and laminates and/or combinations thereof.

The Resilient Member

Resilient member 35 cooperates with the lifting force provided by the angled band 118 to maintain the distal edge 23 of cuff 20 in an elevated configuration relative to the body surface 4A of the topsheet 4. Further, the resilient member 35 resists the compressive forces of the normal wear cycle that can cause the cuffs to collapse.

The resilient member 35 should be large enough to help insure that the cuff 20 acts as an effective barrier to lateral leakage of bodily fluids, yet not so large so as to cause wearer discomfort. Preferably, the resilient member 35 should have a largest cross sectional width of between about 0.04 inches (1 millimeter) and about 0.39 inches (10 millimeters) and a largest cross sectional height between about 0.12 inches (3 millimeters) and about 0.59 inches (15 millimeters).

The resilient member 35 should be soft, yet resilient. That is, the resilient member should be sufficiently resilient to resist the compressive forces encountered during normal bodily movement yet sufficiently soft so as not to be a source of wearer discomfort. The force required to compress the resilient member to 75% of its initial height is between about 100 grams and about 7500 grams. Preferably, the compression force is between about 200 grams and about 4000 grams. More preferably, the compression force is between about 200 grams and about 1500 grams.

Compression force is measured according to ASTM method D 3575-91, Suffix D with the following modifications:

Compression: 75%

Crosshead Speed: 5 inches per minute (127 millimeters per minute)

Tensile Test Instrument: Instron Model 5564, available from Instron Corp. Canton, Mass.

Load Cell: 100 Newton full scale Compression/Tension cell

Gage Length: 0.5 inches (12.7 mm)

Sample: The sample comprised a full cuff rather than the right cylinder described in the ASTM method.

Figure 9:
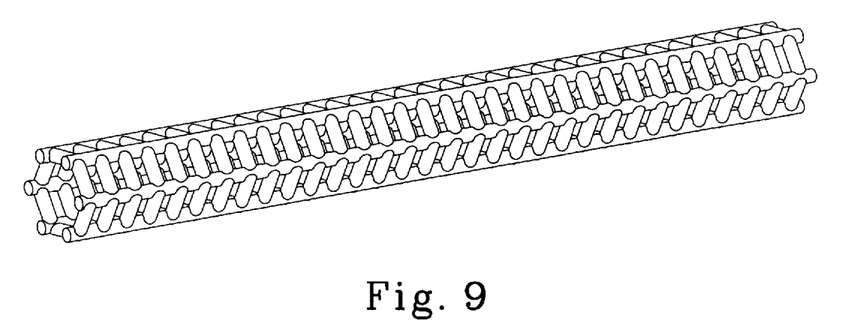
FIGS. 9 to 11 are perspective views of alternative scrim embodiments of the resilient member of the present invention.
Figure 10:
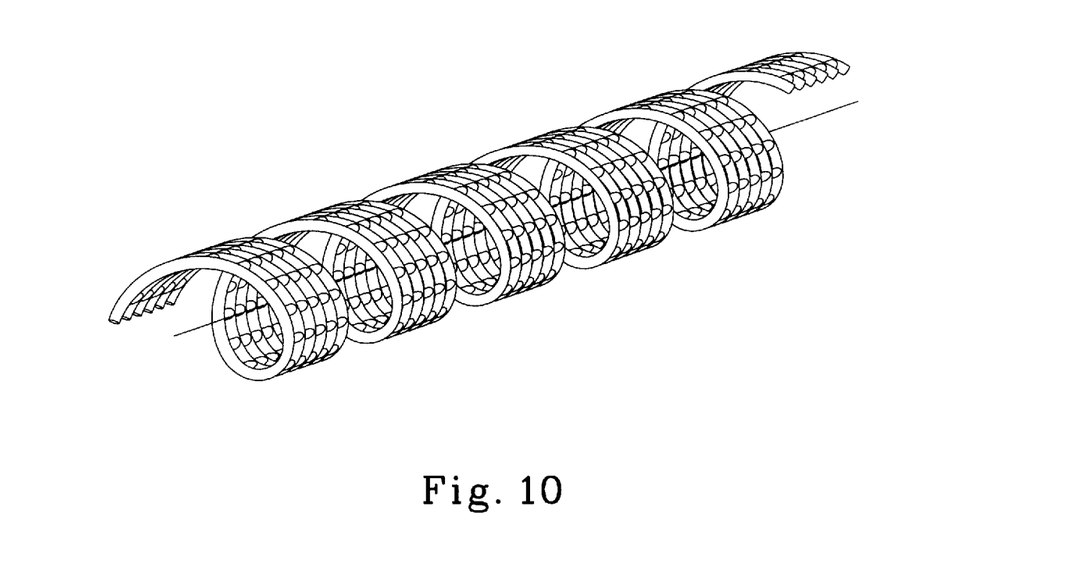
Figure 11:
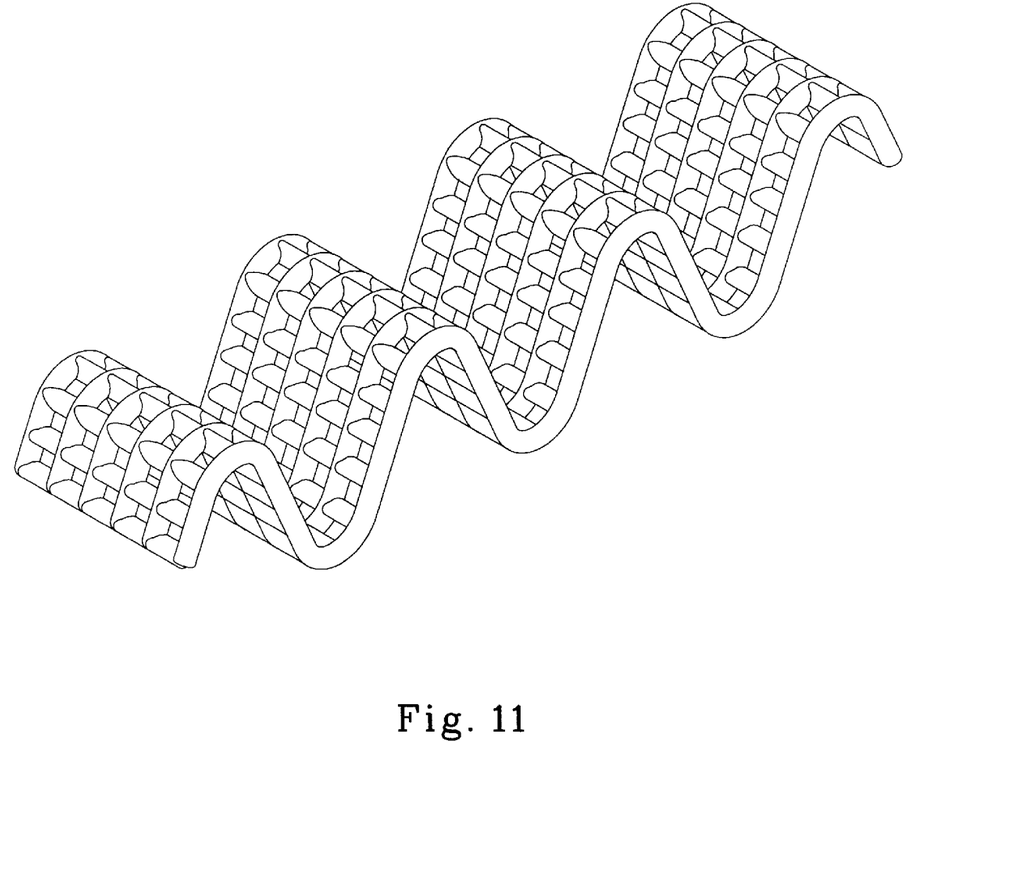

As noted above, the resilient member 35 is soft and resistant to externally applied forces, such as those encountered during normal wear. Any material that resists compression yet is sufficiently soft for wearer comfort is suitable for use as a resilient member. Suitable materials include foams, both blown foams, such as polyurethane foams, and high internal phase emulsion (HIPE) foams as are described in U.S. Pat. No. 5,147,345 issued to Young, et al. on Sep. 15, 1992 are suitable; wet laid and air laid fibrous assemblies, such as the bicomponent (polyethylene/polyester) nonwoven material having a basis weight of about 38 grams per square yard (45.4 grams per square meter) which is available from Veratec of Walpole, Mass. as material number L4-603; and resilient scrim materials that have been formed into a three dimensional configuration (three exemplary configurations for scrim materials: tubular, spiral, and sinusoidal, are shown in FIGS. 9–11). A particularly preferred material for the resilient member 35 is the aforementioned HIPE foam.

Optional Components of the Sanitary Napkin

Flaps

The preferred embodiment of the sanitary napkin 2 of the present invention may also be provided with a pair of flaps. When used, such flaps lie adjacent to and extend laterally outward from each longitudinal edge 5 of the sanitary napkin 2 in the central region 32 thereof. The flaps are preferably configured to drape over the edges of the wearer's panties in the crotch region so that they are disposed between the wearer's panties and the wearer's thighs.

Such flaps can serve at least two purposes. First, the flaps help to prevent soiling of the wearer's body and panties by menstrual fluid or other bodily exudates. Second, the flaps are preferably provided with flap attachment means on their garment surface so that the flaps can be folded back under the panty and attached to the garment-facing side of the panty. In this way, the flaps serve to keep the sanitary napkin 2 properly positioned in the panty. Alternatively, the flaps may be attached to each other on the underside of the panty by the attachment means with or without also being affixed to the panty.

A number of sanitary napkins having flaps suitable or adaptable for use with the sanitary napkin 2 of the present invention are known. Such flaps are disclosed in U.S. Pat. No. 4,285,343, issued to McNair on Aug. 25, 1981; U.S. Pat. No. 4,589,876, issued to Van Tilburg on May 20, 1986; U.S. Pat. No. 4,608,047, issued to Mattingly on Aug. 26, 1986; U.S. Pat. No. 4,687,478 issued to Van Tilburg on Aug. 18, 1987; and in Reexamination Patent B1 4,589,876 issued Apr. 27, 1993. Some particularly preferred types of flaps are described in U.S. Pat. No. 5,281,209 issued to Osborn, et al. on Jan. 25, 1994; in U.S. Pat. No. 5,344,416 issued to Lavash, et al. on Sep. 6, 1994; and in U.S. Pat. No. 5,354,400 issued to Lavash, et al. on Oct. 11, 1994.

The flaps can be constructed of various materials including tissue, woven or nonwoven materials, materials similar to the primary topsheet layer 10, the backsheet 6, or any combination of these materials. Further, the flaps may be a separate element attached to the main body of the sanitary napkin 2 or can comprise extensions of the topsheet 4 and backsheet 6 (i.e., unitary). Preferably, the flaps comprise extensions of the topsheet 4 and the backsheet 6. The extended topsheet 4 and backsheet 6 are joined using means familiar to those skilled in the art. Preferably, the extended topsheet 4 and backsheet 6 are joined about the periphery of the flap by a combination of heat and pressure commonly known as a crimp seal.

To use a sanitary napkin 2 of the present invention, a wearer would first remove any release liner that has been provided and position the sanitary napkin 2 in the crotch region of her panties, insuring that the flaps, if such are provided, are folded over the leg elastics of the panties and that any attachment means provided are used to join the sanitary napkin to the panty. She would then pull the panties on in the normal manner.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a longitudinal centerline defining a longitudinal direction, a pair of opposing side edges, a pair of ends, and a longitudinally extending central portion, said central portion defining a plane, said absorbent article comprising:

a liquid pervious topsheet;

a liquid impervious backsheet joined to said topsheet;

an absorbent core positioned between said topsheet and said backsheet; and a pair of longitudinally extending cuffs, each of said cuffs having a proximal edge and a distal edge, one of said cuffs being disposed adjacent each of said side edges of said absorbent article in a longitudinally elongated state, with said proximal edge of each of said cuffs being joined to at least one of said topsheet or said backsheet, said cuffs comprising:

a resilient member which provides compression resistance and bending resistance to said cuffs; and an elastic member, said elastic member comprising an elastically extensive film material having a first region and a second region, said first and second regions of said elastic member being visibly distinct from each other wherein said second region comprises a plurality of raised rib-like elements and said first region comprises at least two substantially planar regions which provides a contractive force, said elastic member being folded about said resilient member in a C-fold, wherein said contractive force causes said ends to extend upwardly inclinedly away from said plane of said central portion and said distal edges to extend upwardly away from said topsheet along both of said side edges of said central portion.

2. An absorbent article according to claim 1 wherein at least one of said substantially planar first regions is oriented generally in the longitudinal direction, at least one other substantially planar first region is oriented at an angle to said longitudinal direction, and said plurality of raised rib-like elements define ridges that are oriented generally in the transverse direction.

3. An absorbent article according to claim 2 wherein said angle is between about 15 degrees and about 45 degrees.

4. An absorbent article according to claim 1 wherein said resilient member comprises a fibrous assembly.

5. An absorbent article according to claim 4 wherein said fibrous assembly is air laid.

6. An absorbent article according to claim 4 wherein said fibrous assembly is wet laid.

7. An absorbent article according to claim 1 wherein said resilient member comprises a foam.

8. An absorbent article according to claim 7 wherein said foam comprises a HIPE foam.

9. An absorbent article according to claim 7 wherein said foam comprises a blown foam.

10. An absorbent article according to claim 1 wherein said resilient member comprises a scrim.

11. An absorbent article according to claim 10 wherein said scrim has been rolled about a longitudinally extending axis such that it has a cylindrical configuration.

12. An absorbent article according to claim 10 wherein said scrim has been wrapped about a longitudinally extending axis in a spiral configuration.

13. An absorbent article according to claim 10 wherein said scrim has been provided with a sinusoidal configuration.

14. An absorbent article having a longitudinal centerline defining a longitudinal direction, a pair of opposing side edges, a pair of ends, and a longitudinally extending central portion, said central portion defining a plane, said absorbent article comprising:

a liquid pervious topsheet;

a liquid impervious backsheet joined to said topsheet;

an absorbent core positioned between said topsheet and said backsheet; and a pair of longitudinally extending cuffs, each of said cuffs having a proximal edge and a distal edge, one of said cuffs being disposed adjacent each of said side edges of said absorbent article in a longitudinally elongated state, with said proximal edge of each of said cuffs being joined to a least one of said topsheet or said backsheet, said cuffs comprising:

a resilient member which provides compression resistance and bending resistance to said cuffs, wherein said resilient member comprises a foam; and an elastic member comprising a SELF web, which provides a contractive force when elongated, said elastic member being folded about said resilient member in a C-fold, wherein said contractive force causes said ends to extend upwardly inclinedly away from said plane of said central portion and said distal edges to extend upwardly away from said topsheet along both side edges of said central portion.

15. An absorbent article according to claim 14 wherein said absorbent article further comprises a pair of laterally extending flaps, wherein a flap is joined to each of said side edges in at least said central region and said extends outward therefrom in a lateral direction.

* * * * *